United States Patent
Schuele et al.

(10) Patent No.: US 7,767,411 B2
(45) Date of Patent: Aug. 3, 2010

(54) ASSAY SYSTEM FOR SPECIFIC INHIBITORS OF PROTEIN KINASE C-RELATED KINASES

(75) Inventors: Roland Schuele, Weisweil (DE); Eric Metzger, Neuf Brisach (FR)

(73) Assignee: Universitaetsklinikum Freiburg, Freiburg (DE)

( * ) Notice: Subject to any disclaimer, the term of this patent is extended or adjusted under 35 U.S.C. 154(b) by 386 days.

(21) Appl. No.: 10/592,313

(22) PCT Filed: Mar. 10, 2005

(86) PCT No.: PCT/EP2005/002554

§ 371 (c)(1), (2), (4) Date: Dec. 13, 2006

(87) PCT Pub. No.: WO2005/095957

PCT Pub. Date: Oct. 13, 2005

(65) Prior Publication Data

US 2007/0196882 A1     Aug. 23, 2007

(30) Foreign Application Priority Data

Mar. 11, 2004 (EP) .................................. 04005833

(51) Int. Cl.
*C12Q 1/48* (2006.01)
(52) U.S. Cl. ........................................ 435/15; 435/69.2
(58) Field of Classification Search .................... 435/15, 435/69.2
See application file for complete search history.

(56) References Cited

U.S. PATENT DOCUMENTS

2005/0283841 A1* 12/2005 McKinsey et al. ............. 800/3

OTHER PUBLICATIONS

Metzer E. et al. A Novel Inducible Transactivation Domain in the Androgen Receptor: Implications for PRK in Prostate Cancer. The EMBO Journal 22(2)270-280, 2003.*
Metzger E. et al. A Novel Inducible Transactivation Domain in The Androgen Receptor. The EMBO Journal 22(2)270-280, Jan. 15, 2003.*
Davies S. et al. Specificity and Mechanism of Action of Some Commonly Used Protein Kinase Inhibitors. Biochemistry Journal vol. 351 pp. 95-105, 2000.*
E. Metzger et al., The EMBO Journal, 2003, vol. 22, No. 2, pp. 270-280, XP-001182138.
S.-J. Lee et al., Developmental Biology, 2000, vol. 228, pp. 166-180, XP-002286096.
M. Standaert et al., The Journal of Biological Chemistry, 1998, vol. 273, pp. 7470-7477, XP-002286097.
C. Yoshinga et al., J. Biochem., 1999, vol. 126, pp. 475-484, XP-001189682.
S.P. Davies et al., Biochemical Journal, 2000, vol. 351, pp. 95-105, XP-009014248.
A. Balendran et al., The Journal of Biological Chemistry, 2000, vol. 275, No. 27, pp. 20806-20813, XP-000925909.
E. Sahai et al., The EMBO Journal, 1998, vol. 17, No. 5, pp. 1350-1361, XP-002286098.
P. Flynn et al., The Journal of Biological Chemistry, 1998, vol. 273, No. 5, pp. 2698-2705, XP-002286099.

* cited by examiner

*Primary Examiner*—Ralph Gitomer
(74) *Attorney, Agent, or Firm*—Greenblum & Bernstein P.L.C.

(57) ABSTRACT

The present invention relates to an assay system for specific inhibitors of protein kinase C-related kinases (PRKs) relating to one or more of the reactions wherein said protein kinase C-related kinases are involved under physiological conditions. The invention also relates to a process for identifying specific inhibitors for protein kinase C-related kinases.

16 Claims, 3 Drawing Sheets

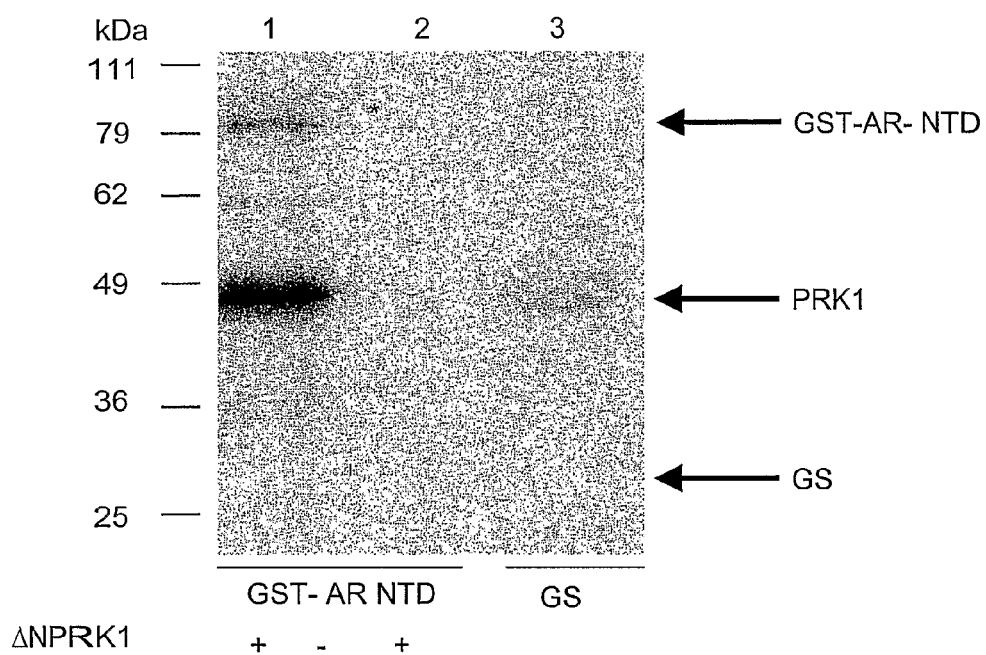
Figure 1: PRK1 phosphorylates AR-NTD *in vitro*.

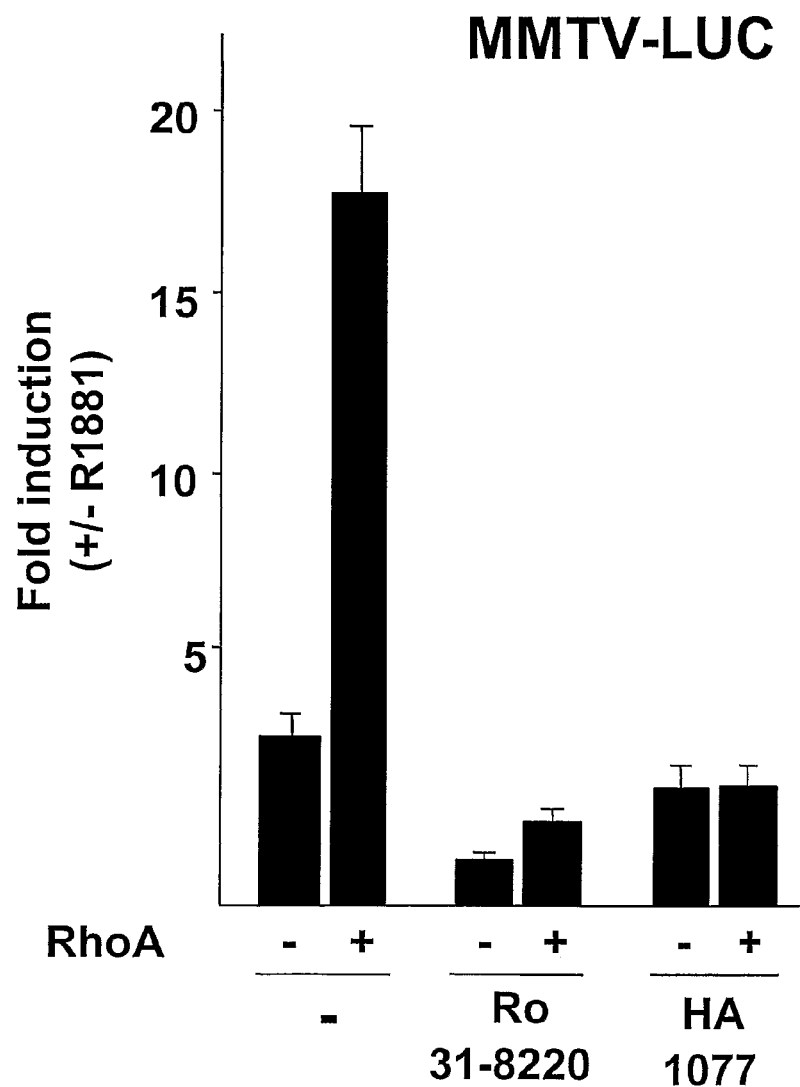
Figure 2: Ligand-dependent activation of AR by RhoA V14 is blocked by the PRK inhibitors Ro31-8220 or HA 1077.

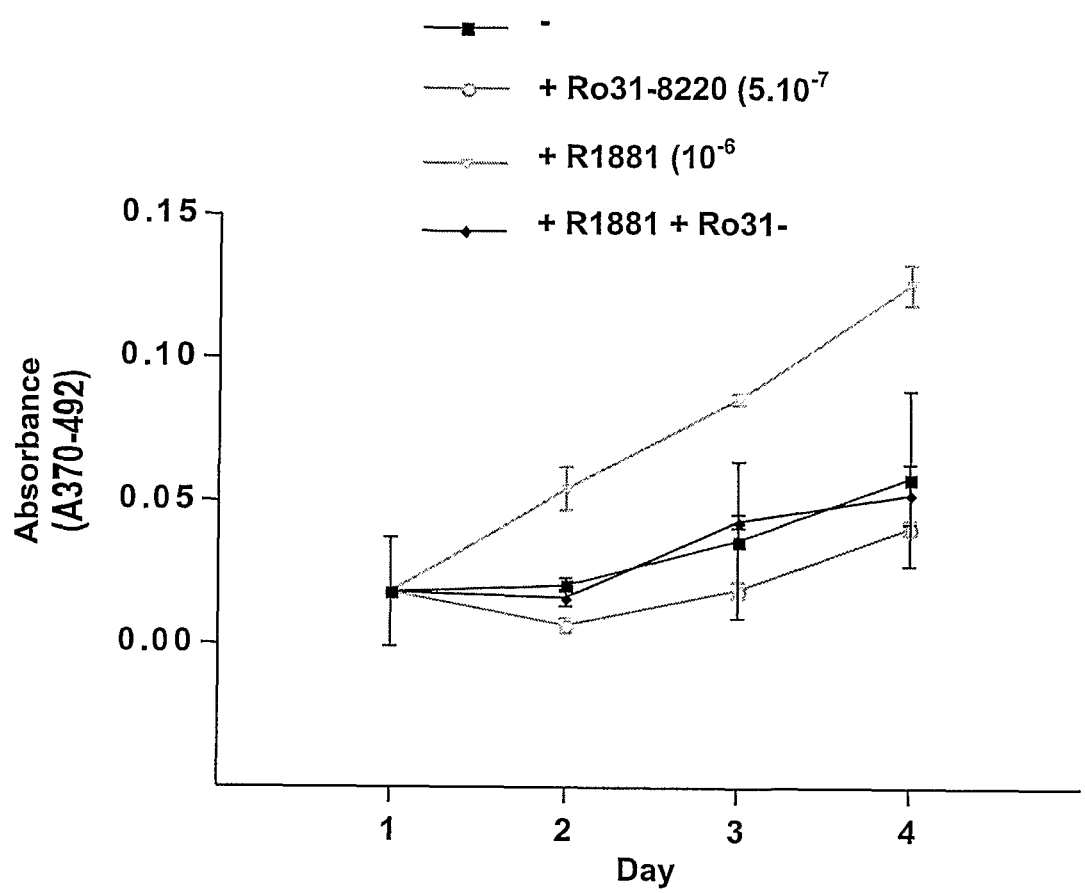
Figure 3: The PRK inhibitor Ro31-8220 blocks the androgen R1881 induced MCF-7

ASSAY SYSTEM FOR SPECIFIC INHIBITORS OF PROTEIN KINASE C-RELATED KINASES

CROSS-REFERENCE TO RELATED APPLICATIONS

The present application is a U.S. National Stage of International Application No. PCT/EP2005/002554, filed Mar. 10, 2005, which claims priority of European Patent Application No. 04 005 833.1, filed Mar. 11, 2004.

BACKGROUND OF THE INVENTION

1. Field of the Invention

The present invention relates to an assay system for specific inhibitors of protein kinase C-related kinases.

Furthermore, the present invention relates to a process for testing protein kinase inhibitors for their specificity. The invention also relates to the use of an assay system in testing protein kinase inhibitors for their specificity.

2. Discussion of Background Information

The androgen receptor (AR) is a member of the steroid hormone receptor family of transcription factors which regulate diverse biological functions including cell growth and differentiation, development, homeostasis and various organ functions in a mammal, particularly in a human. By binding suitable ligands like androgens to the ligand binding domain, functions of the AR are activated which are essential for the differentiation, development and maintenance of male or female reproductive organs and non-reproductive organs (as, for example, the prostate or the mammae).

It is known that, in the prostate, the AR is expressed in secretory epithelial cells that respond to androgens. As presently acknowledged, the growth and survival of primary prostate cancer cells is critically dependent upon androgens, and hence, the AR plays an important role in the development of prostate cancer, on the one hand, and in strategies of inhibiting prostate tumor growth and preventing a tumor recurrence, on the other hand. However, reducing the androgen level in a mammal/human in the course of the usual anti-prostate cancer androgen ablation therapy or even administering AR antagonists did not result in a reliable inhibition of prostate tumor growth or prevention of tumor recurrence. This finding led to the conclusion that the activity of the AR is not (or at least not exclusively) stimulated or inhibited by binding ligands (like androgens or AR antagonists) to the AR ligand binding domain, but may be regulated by an inter-action of the AR with other (even extracellular) signaling molecules. E. Metzger, J. M. Müller, S. Ferrari, R. Buettner and R. Schüle (The EMBO Journal 22 (2003), 270-280 with further references) found that the transcriptional activation of the AR can be linked to protein kinase C-related kinases (PRKs). Furthermore, these authors demonstrate the in vivo relevance of this pathway for promoting metastasis of prostate tumours in immunocompetent animals, especially bone-directed metastasis commonly associated with advanced prostate cancer.

The PRKs constitute a subfamily of serine/threonine kinases which includes PRK1, amongst others. PRK1 activates the AR by binding to its transactivation unit 5 (TAU-5). Hence, PRK1 signalling can result into an activation of the AR even in the absence of androgens or in the presence of AR antagonists (as, for example, cyproterone acetate). This fact explains why even in the absence of androgens or in the presence of androgen antagonists (resulting usually into a lack or even prevention of the AR activation via binding to the ligand binding domain of the AR), the AR can be activated or, as was recently found, activated even more than in the situation where an androgen is bound to the ligand binding domain, with the consequence that growth and survival of primary prostate cancer cells is promoted, sometimes even more promoted than in a situation where the AR stimulates the cell growth. Hence, blocking the PRK1 signalling pathway by a suitable PRK1 inhibitor should result into an inhibition of the AR activity and, hence, to an inhibition of the deleterious growth of prostate cancer cells.

It is known that the enzymatic action of protein kinases can be controlled or even inhibited by a number of known inhibitors. However, the protein kinase inhibition was shown to lack the desired specificity. Although in recent years several small, cell-permeant inhibitors of protein kinases (including inhibitors of protein kinase C-related kinases like PRK1) were developed that exhibit a relatively high specificity for a particular protein kinase, the known inhibitors still inhibited two or more protein kinases with similar potency, resulting in an unspecific protein kinase inhibition (S. P. Davies, H. Reddy, M. Caivano and P. Cohen, Biochem. J. 351 (2000), 95-105). Hence, the necessary specificity of the protein kinase inhibition by high specificity inhibitors, although keenly desired and sought for, could not be achieved up to now.

It was an object of the invention to provide an assay system for identifying specific inhibitors of protein kinase C-related kinases.

It was another object of the invention to provide a process for testing protein kinase inhibitors for their specificity.

Furthermore, it was an object of the invention to provide a use of an assay system in testing protein kinase inhibitors for their specificity.

Also, it is an object of the invention to corroborate the high specificity protein kinase C-related kinase inhibitors designated using an in vivo test system that includes a metastasizing prostate tumor growing in an immunocompetent mammal.

Surprisingly, it was now found by the present inventors that, with a system of assays, protein kinase inhibitors can be tested for their specificity, thus allowing specificity tests to be performed easily on a large number of compounds potentially being considered suitable inhibitors of protein kinases, in particular inhibitors of protein kinase C-related kinases, with the aim of discovering highly specific inhibitors of protein kinase C-related kinases (PRKs) allowing to selectively block the activity of nuclear receptors as, for example, the androgen receptor (AR).

SUMMARY OF THE INVENTION

The present invention provides an assay for identifying a specific inhibitor of a protein kinase C-related kinase (PRK). The assay comprises at least one reaction in which the PRK is involved under physiological conditions.

In one aspect of the assay, the PRK may comprise at least one of PRK1, PRK2 and PKNβ. For example, the PRK may comprise PRK1.

In another aspect, the assay may comprise at least two independent reactions in which the PRK is involved under physiological conditions. For example, the assay may comprise at least two reactions which are acted upon by the PRK under physiological conditions.

In yet another aspect, the assay may comprise at least one reaction which is promoted by the PRK under physiological conditions and/or may comprise a phosphorylation of the N-terminal domain of the androgen receptor (AR-NTD) by PRK1 and/or may comprise a ligand-dependent activation of the androgen receptor by RhoA V 14 and/or may comprise a promotion of an androgen receptor agonist-induced cell proliferation by the androgen receptor and/or may comprise at least one reaction which is prevented or blocked by the PRK under physiological conditions.

The present invention also provides a process for identifying a specific inhibitor of a protein kinase C-related kinase (PRK). The processes comprises the provision of at least one reaction system which involves at least one PRK and allowing the at least one PRK to exert at least one measurable effect in the at least one reaction system under physiological conditions; the addition of distinguishable effective amounts of a substance to be tested with respect to its PRK inhibitory activity to the at least one reaction system; and the measurement of the at least one measurable effect as a function of the distinguishable effective amounts of said substance to determine the presence of an inhibitory effect thereof.

In one aspect of the process, the PRK may comprise at least one of PRK1, PRK2 and PKNβ. For example, the PRK may comprise PRK1.

In another aspect of the process, the reaction system may comprise at least two independent reactions in which the PRK is involved under physiological conditions. For example, the reaction system may comprise at least two reactions which are acted upon by the PRK under physiological conditions.

In yet another aspect, the reaction system may comprise at least one reaction which is promoted by the PRK under physiological conditions and/or may comprise a phosphorylation of the N-terminal domain of the androgen receptor (AR-NTD) by PRK1 and/or may comprise a ligand-dependent activation of the androgen receptor by RhoA V 14 and/or may comprise a promotion of an androgen receptor agonist-induced cell proliferation by the androgen receptor and/or may comprise at least one reaction which is prevented or blocked by the PRK under physiological conditions.

The present invention also provides a method of searching or screening for substances which are highly specific inhibitors of a protein kinase C-related kinase (PRK). The method comprises using an assay or assay system for identifying specific inhibitors of the PRK.

The present invention also provides a method of influencing an androgen receptor. The method comprises (i) blocking the ligand-activated stimulation of the androgen receptor at its ligand binding domain and (ii) blocking the protein kinase C-related kinase (PRK)-activated stimulation of the androgen receptor via its transcription activation unit (TAU-5).

In one aspect of the method, (ii) may comprise a blocking of the PRK-activated stimulation by one or more inhibitors of one or more protein kinase C-related kinases.

The present invention also provides a method of treating prostate cancer. The method comprises (i) blocking the protein kinase C-related kinase-activated stimulation of the androgen receptor via its transcription activation unit (TAU-5) and (ii) reducing the level of circulating androgen and/or (iii) increasing the level of antagonist of the androgen receptor.

In one aspect of the method, (i) may comprise the blocking of the protein kinase C-related kinase-activated stimulation by one or more inhibitors of one or more protein kinase C-related kinases. For example, the one or more inhibitors may comprise an inhibitor with high specificity.

The present invention also provides a method of treating prostate cancer, which method comprises the blocking of a protein kinase C-related kinase-activated stimulation of the androgen receptor via its transcription activation unit (TAU-5) by using one or more high specificity inhibitors of one or more protein kinase C-related kinases.

BRIEF DESCRIPTION OF THE DRAWINGS

FIG. 1 shows a chromatograph obtained by conducting the AR-NTD phosphorylation assay described in Example 1 below.

FIG. 2 is a bar representation showing the results of the assay described in Example 2 below regarding the blocking of the ligand-dependent activation of the androgen receptor (AR).

FIG. 3 is a graph representing the results of the cell proliferation assay described in Example 3 below.

DETAILED DESCRIPTION OF THE INVENTION

The invention relates to an assay system for identifying specific inhibitors for protein kinase C-related kinases (PRKs) relating to one or more of the reactions wherein said protein kinase C-related kinases are involved under physiological conditions.

Furthermore, the invention also relates to a process for identifying specific inhibitors for protein kinase C-related kinases (PRKs), said process comprising the steps of selecting a substance to be tested for its protein kinase C-related kinase inhibitor capacity;

providing at least one reaction system involving at least one protein kinase C-related kinase and allowing said at least one protein kinase C-related kinase to exert at least one measurable effect in said at least one reaction system under physiological conditions;

adding distinguishable effective amounts of said substance to be tested to said at least one reaction system so as to obtain an inhibitor effect of said inhibitor on said protein kinase C-related kinase in said at least one reaction system; and measuring said measurable effect in dependency upon the distinguishable effective amounts of said substance to be tested so as to ascertain an inhibitory effect of said substance to be tested on said at least one protein kinase C-related kinase in said at least one reaction system.

The invention also relates the use of assays or assay systems for identifying specific inhibitors for protein kinase C-related kinases (PRKs) for the searching for, or screening for, substances which may be found to be suitable highly specific inhibitors for protein kinase C-related kinases (PRKs).

The invention also relates to a process for adding, to the blocking of the ligand activated stimulation of the androgen receptor at its ligand binding domain, a blocking of the protein kinase C-related kinase (PRK)-activated stimulation of the androgen receptor via its transcription activation unit (TAU-5) by inhibitors of the protein kinase C-related kinases (PRKs) with high specificity.

The invention also relates to the use of high specificity inhibitors of protein kinase C-related kinases (PRKs) for blocking the protein kinase C-related kinase (PRK)-activated stimulation of the androgen receptor via its transcription activation unit (TAU-5) with high specificity.

The invention also relates to the use of high specificity inhibitors of protein kinase C-related kinases (PRKs) for the manufacture of a medicament for blocking the protein kinase C-related kinase (PRK)-activated stimulation of the androgen receptor via its transcription activation unit (TAU-5) with high specificity, permitting the preclinical corroboration of said medicament in vivo in an immunocompetent mammal.

Furthermore, the invention relates to a process for the treatment of prostate cancer by adding, to the reduction of the circulating androgen level and/or to the increase of the AR antagonist level, the step of blocking the protein kinase C-related kinase (PRK)-activated stimulation of the androgen receptor via its trandrogen scription activation unit (TAU-5) by inhibitors of the protein kinase C-related kinases (PRKs) with high specificity, permitting the preclinical corroboration of said high specificity inhibitors in vivo in an immunocompetent mammal.

In addition, the invention relates to the use of high specificity inhibitors of protein kinase C-related kinases (PRKs) for the treatment of prostate cancer by blocking the protein kinase C-related kinase (PRK)-activated stimulation of the androgen drogen receptor via its transcription activation unit (TAU-5) with high specificity.

The invention also relates to the use of high specificity inhibitors of protein kinases nase C-related kinases (PRKs) for the manufacture of a medicament for the treatment of prostate cancer by blocking the protein kinase C-related kinase (PRK)-activated stimulation of the androgen receptor via its transcription activation unit (TAU-5) with high specificity.

In accordance with the invention, the assay system, the process for identifying certain substances and the use of the assay system as well as the process for the additional blocking and the uses of high specificity inhibitors are applicable to substances occurring in or derived from mammals or relate to mammals, respectively, although any assay system usually is not applied directly to a mammal. Mammals are broadly defined for the purpose of the present invention as vertebrates having warm blood, having a skin which is at least partly covered with hair and nourishing their young ones with milk from mammae, udders or breasts. In particularly preferred embodiments of the invention, the mammals from which the substances and systems are derived are humans. In accordance with the definition of mammals, specifically humans, the term "physiological conditions" is understood to mean conditions which allow a mammal or, specifically, a human to exist and to be under acceptable living conditions without any undue burden concerning temperature, pressure, acidity/basicity, humidity/aqueous conditions of liquid systems, oxygen content of the gaseous environment etc. In addition, the invention relates to the use of high specificity inhibitors of protein kinase C-related kinases (PRKs) for the treatment of prostate cancer in said mammals, being employed as preclinical models of metatasizing prostate cancer, by blocking the protein kinase C-related kinase (PRK)-activated stimulation of the androgen receptor via its transcription activation unit (TAU-5) with high specificity.

In accordance with the invention, the term "assay" or "assay system" as used in the description and claims is understood to mean substances, usually a plurality of substances, useable and used for conducting tests, e. g. tests for checking or establishing properties of substances in question (or, in certain cases, also a plurality of substances in question) in accordance with a routine or schedule which is proposed in the design of the assay or test. The term "assay" or "assay system" in accordance with the present invention is also intended to cover optional commercially available kits which include not only the substance(s) to be used, but also optional devices sometimes provided by the manufacturer for use together with the substance(s) as well as any written material showing the manner how to proceed when successfully applying the assay or assay system to a certain test to be conducted.

In accordance with the invention, the substances sought for are inhibitors of protein kinase C-related kinases. The term "protein kinase C-related kinases", hereinafter also abbreviated as "PRKs", is meant to include, in a broad sense, the subfamily of serine/threonine kinases which are included in signalling cascades, can be activated by extracellular signals and can be blocked by chemical compounds designed as inhibitors. In addition, they act on target proteins by phosphorylating serine and/or threonine residues. The term particularly includes PRK1 (also called PKN), PRK2 and PKNβ. The assay systems of the invention particularly address the inhibition of those PRKs which effect a blocking of the transcriptional activity of mammalian nuclear receptors with high specificity. In a preferred embodiment of the invention, the mammalian nuclear receptors the transcriptional activity of which is blocked are human nuclear receptors. The nouns "inhibitor" and "inhibition" and the verb "inhibiting" as used in the present description and claims are understood to mean, in the broadest sense, a substance or an activity of such a substance which relates to a deceleration (decrease in activity) or a complete prevention, stopping or interruption of the activity.

The term "blocking" is understood to mean, in the present description and claims, any influence of the enzyme on the activity of the nuclear receptor which decelerates the speed or decreases the efficiency of the nuclear receptor. This deceleration or decrease may include the case (which case is, of course, preferred) where the activity of the nuclear receptor is directly influenced, particularly directly reduced to substantially zero, by an inhibition of the enzyme but also includes the case where the enzyme has an effect, for example as an effector, on previous stages of the cascade activating (or inactivating) the nuclear receptor and, thus, indirectly decelerates or decreases the receptor activity. In particularly preferred embodiments, such a blocking may occur in parallel directly and indirectly.

In preferred embodiments of the invention, the blocked activity of the nuclear receptor is a transcriptional activity. Transcriptional activity is understood to mean, in the present description and claims, a transcriptional repression or transcriptional activation, while in the understanding of the present invention, the blocking effect of the inhibitors results in a transcriptional repression or transcriptional inactivation.

The term "high specificity" as used in the present description and claims, is understood to mean herein that, in contrast to many kinase inhibitors of the prior art, the inhibitors of protein kinase C-relates kinases (PRKs) sought for by the assay of the present invention do not act on a great number or on two or more protein kinases having similar potency, but act specifically (i. e. only) on PRKs, more preferably act specifically (i. e. only) on PRK1, PRK2 and/or PKNβ, even more preferably act specifically (i. e. only) on PRK1 . Hence, the situation (described, for example, in S. P. Davies et al., loc. cit.) that inhibitors like Y 27632 act on PRKs, but also on MSK1, ROCK-II and MAPKAP-K1b, or Ro 318220 act on PRKs, but also on MSK1, S6K1 and other protein kinases, will not occur with the inhibitors sought for by the assay of the present invention which are desired exhibit a high specificity for PRKs, particularly for PRK1 . In a most preferred embodiment of the invention, the specificity of the inhibitors is given by the $IC_{50}$ value. The $IC_{50}$ value is defined as the concentration of inhibitor required to inhibit 50% of the PRK activity. A moderately specific inhibitor for protein kinase C-related kinases (PRKs) should have an $IC_{50}$ value >10 nM, while the highly specific inhibitors sought for by means of the assay system of the present invention should be designed to have an $IC_{50}$ value<10 nM.

Substances tested with the assay systems of the present invention and expected to be inhibitors should be inhibitors of one protein kinase C-related kinases (PRK) which effect, with high specificity, a blocking of the transcriptional activity of mammalian nuclear receptors. In a preferred embodiment, the inhibitors sought for should be specific inhibitors of one PRK which is selected from the group consisting of PRK1, PRK2 and PKNβ.

In accordance with the invention, there is provided an assay system for identifying specific inhibitors for protein kinase C-related kinases (PRKs) relating to one or more of the reactions wherein said protein kinase C-related kinases are involved under physiological conditions.

The step of identifying substances as specific inhibitors of PRKs is understood to mean in the present description and claims the searching for substances which might be specific inhibitors, the pre-evaluation, due to apparent parameters which may include, but are not limited to structure or certain structural features, conformation, acidity/basicity or other parameters known to a person skilled in this technical field, the screening of substance data bases etc., the step of deciding that a substance or group of substances in subjected to a later assay or series of assays, the application of the assay or series of assays or system of assays, respectively, to said substance or group of substances, and finally the corroboration in vivo of said substance or group of substances in a preclinical immunocompetent model mammal harbouring a metastasizing prostate tumour.

Reactions which are suitable for the assay or assay system of the invention may be single reactions, which are used in the way of one single reaction in one assay. The term "reaction" or "at least one reaction" may be understood to mean not only one single conversion of one substance or a pair of substances, but may also be understood in the sense of a reaction sequence or "cascade" which is the basis of one assay. In order to have a substance properly checked for its inhibitory capability, it may be desired and, even preferred that several, i. e. two or more than two, single reactions are carried out in separate and distinguishable assay so as to ensure the desired suitability of the substance as an inhibitor of protein kinase C-related kinases (PRKs). Such distinguishable assay all having the same aim but being based on different chemical reactions may be called an assay system of the present invention. It is preferred in accordance with the invention that several distinguishable chemical reactions are employed, i. e. several assays are finally put together to form an assay system of the invention which allows a quick and reliable testing of whether a substance is a high selectivity inhibitor of PRKs and a rapid, reliable corroboration in vivo of putative inhibitors so designated.

A preferred embodiment of the invention is directed to an assay system which comprises at least two independent reactions wherein said protein kinase C-related kinases are involved under physiological conditions. Assay systems consisting not only of one but of at least two independent reactions are preferred due to their better reliability in finding suitable substances as inhibitors for PRKs. In particular, the passage of two independent reactions ensures a better selection of substances which might have the desired high specificity towards protein kinase C-related kinases like PRK1, PRK2 and PKNβ. Details of exemplary reactions which are applied to substances in question independently are, for example, the AR-NTD phosphorylation assay, the ligand-dependent activation of the androgen receptor (AR) by RhoA V 14 and the androgen receptor agonist R 1881-induced cell proliferation in MCF-7 cells.

In further preferred embodiments of the invention, the assay system comprises at least two reactions acted upon by the protein kinase C-related kinases under physiological conditions which the assay system comprises. As can be seen from the exemplary embodiments mentioned above, the reactions involve the preferred protein kinase C-related kinases (PRKs), specifically PRK1, which act upon substances included into said reaction under physiological conditions. In one of the preferred embodiments, which can be in detail seen from Example 1, the PRK1 acts on the androgen receptor (AR) in a way phosphorylating it; the phosphorylation reaction results into an activation of the AR. This reaction may be taken as a basis for an assay for the specificity of substances inhibiting the PRK1 protein kinase: An inhibition of the PRK with high specificity (i. e. without inhibiting other protein kinases) would result into an inactivation of the PRK1, which-in turn-results into the situation that the AR is not phosphorylated, i. e. remains inactive. Inhibitors achieving this with specificities<10 nM could be named to be highly specific inhibitors of PRK1.

In accordance with the invention, it is preferred that said assay system comprises at least one reaction promoted by the protein kinase C-related kinases under physiological conditions. The term "promoting" or "promotion" as used in the present description and claims is understood to mean that the reaction used for the assay, i. e. at least one reaction used for the assay, is a chemical reaction where the protein kinase C-related kinase (PRK) is in its active state and is active in activating the molecule under physiological conditions to its action in the metabolism. In other words: The reaction (i. e. at least one reaction) on which the assay is based is a reaction activating the molecules of the cascade to an improved (or accelerated) action.

To give detailed examples of such an activating or promoting action, reference is again made to the working examples which give three examples of a promoting action, by the enzyme (i. e. protein kinase C-related kinase, PRK), on the molecules used in the cascade for the assay Examples 1, 2 and 3). Of course, if the promoting or activating action of the PRK on the molecule(s) subsequent in the cascade is inhibited, the activating action on the target molecule is missing. Hence, the target molecule of the enzyme (within the cascade or chemical reaction) is not activated, which missing activation is the indicator for the effective inhibition by the inhibitor, which is sought for the high specificity inhibitor substances with the assay system of the present invention.

In another preferred embodiment, the assay system comprises the reaction of the ligand-dependent activation of the androgen receptor (AR) by RhoA V 14. It could be shown that, in the case of the androgen receptor, the RhoA V 14-mediated activation is dependent upon the presence or absence of an androgen receptor (AR) agonist as, for example, R1881. PRKs are involved in such an activation of the AR in the sense of an activation or promotion, and an inhibition by a potent inhibitor would reliably block such an activating or promoting action of the PRKs. Reference is made, in this respect, to Example 2 and FIG. 2. It could be shown by a use of known inhibitors that such a reaction "cascade" can be used as the basis for an assay on the inhibitory potency of inhibitors towards PRKs.

It is a further preferred embodiment of the invention (and another example of a promoting action of the PRKs) that the assay system comprises the reaction of promotion of the androgen receptor agonist-induced cell proliferation by the androgen receptor. The inventors studied the cell proliferation inter alia in MCF-7 cells which is induced by the androgen receptor agonist R 1881 under the activating/promoting action of PRKs. It could be shown, too, by use of a known inhibitor of PRKs that such a reaction "cascade" is inhibited by the inhibitor action on PRK and, hence, that such inhibitor action can be used as a basis for an assay on the inhibitory potency of inhibitors towards PRKs.

According to an alternative embodiment of the invention, the assay or assay system according to the invention comprises at least one reaction prevented or blocked by the protein kinase C-related kinases under physiological conditions. In this case, as in the other embodiments, one single reaction may be used, or a sequence or cascade of reactions or even several reactions of the same or different types may be used. It is preferred that one or two reactions are employed. However, the action of the at least one PRK, preferably one PRK, is not a promoting or activating action but is a preventing or even blocking action. If the PRK (for example blocking a reaction) is inhibited itself by a potent inhibitor, it blocking action is not prevailing, and the reaction may proceed without the block formerly preventing the reaction.

The invention also relates to a process for identifying specific inhibitors for protein kinase C-related kinases (PRKs). With respect to this process, the terms "identifying", "PRKs" and "inhibitor specificity" were already explained and defined above and need no further explanation here.

The process of the invention comprises the steps of
selecting a substance to be tested for its protein kinase C-related kinase inhibitor capacity;
providing at least one reaction system involving at least one protein kinase C-related kinase and allowing said at least one protein kinase C-related kinases to exert at least one measurable effect in said at least one reaction system under physiological conditions;
adding distinguishable effective amounts of said substance to be tested to said at least one reaction system so as to obtain an inhibitor effect of said inhibitor on said protein kinase C-related kinase in said at least cane reaction system; and
measuring said measurable effect in dependency upon the distinguishable effective amounts of said substance to be tested so as to ascertain an inhibitory effect of said substance to be tested on said at least one protein kinases C-related kinase in said at least one reaction system.

With respect to the substances to be tested, there is basically no restriction to a skilled person to include any substance in the screening or test or assay. In particular, substances like Ro31-8220 or HA 1077 which are already known as protein kinase C-related kinase inhibitors may be used; however, it has to be considered that those inhibitors have only a low specificity (>10 nM) and show an inhibitory effect on a number of protein kinases so that they are useable, but less advantageous in an overall view.

In the next step, at least one reaction system involving at least one protein kinases C-related kinase is provided. With respect to the term "at least one", reference is made to the explanations above, and there may be one single reaction, a reaction sequence or cascade or a number of reactions simultaneously or separately which may be provided. The term "provided" as mentioned in the description and claims is understood to mean that the apparatus, chemical reagents, solvents, auxiliary substances, gases, energy etc. are provided in suitable amounts and purities, and that all preparations are made to make the reaction or reactions to proceed. This will include, as will be appreciated by a skilled person, the start of the reaction in order to approach an equilibrium in cases where this has to occur before the enzymatic components are added, or the removal of aliquots of the reaction system for analytic or other purposes in cases where this is required.

As soon as all these preparations are made, the reaction is started as usual, which means that the at least one enzymatic component, i. e. the protein kinase C-related kinase(s) [PRK(s)], is/are added, if this was not yet done before. One PRK may be used, or several PRKs may be used; the former case is preferred. Dependent upon the respective basic reaction of the assay or assay system, the PRK(s) is/are exerting an effect on the reaction, e. g. an activating/promoting effect or a decelerating or preventing effect. This situation includes the case that, due to the enzyme intervention, no effect is shown at all (prevention of the reaction due to the enzyme action). Usually, such an effect exerted by the enzyme is measurable in the assay system or assay selected, i. e. the assay system or assay is set up in a way allowing the measurement of the enzyme action. Particularly the physiological conditions are a vital precondition for such an effect measurable in the assay of the invention.

The above conditions of providing the at least one reaction system are easily and conveniently met, for example, in cases where so-called assay kits are used. Such kits are often provided by manufacturers or companies developing the assay and contain all or the majority of the necessary chemical reagents and, in some cases even the devices in which or by means of which the assay is to be performed or is proposed to be performed and any necessary information that may be helpful for performing the assay. Of course, the provision of the assay in the form of a kit is included in the present invention.

The next step of the process of the invention, i. e. the addition of the proposed enzymatic inhibitor, may be performed after the step of providing the chemicals and devices and, even, after the step of starting the reaction, for example for reaching an equilibrium, or said step may be performed simultaneously with the steps explained above. In the latter case, the substance expected to inhibit the enzyme is already added to the reaction system (assay) together with all (or a part) of the chemicals needed for the reaction. This order of combining the reactants may be selected by a skilled person dependent upon the case, and there are no restrictions in this respect. A skilled person may obtain the necessary guidance in suitable textbooks, in the kit manufacturers' advice or on the basis of his skill in similar cases of reacting substances under physiological conditions.

Also the amount of substance expected to be an inhibitor of the PRK(s) can easily be established by a skilled person. The amount will in any case be an effective amount, i. e. an amount which acts in the assay in the desired way, i. e. interacts with the PRK(s) in the at least one chemical reaction. Usually, there are added distinguishably different amounts of said substance to several identical embodiments of the assay in order to obtain a dose-dependency or concentration dependency of the effect achieved by said substance. "Effective amount", in a preferred embodiment, is understood to mean that the desired inhibitory effect on the PRK(s) is not only obtained but can also be subjected to a suitable, reliable and reproducible measurement.

In a preferred embodiment, the concentration-dependency is recorded for the inhibitory effect which exhibited by the inhibitor with respect to the PRK enzyme(s). Thereby, an inhibitory effect of said substance, subject to the assay, on said at least one protein kinase C-related kinase (PRK) in said at least one reaction system is ascertained.

With respect to the preferred embodiments of the process of the invention, reference is made to the explanations of the assay or assay system, respectively, and the disclosure is similarly applicable to the preferred embodiments of the present process.

The invention also relates to the use of assays or assay systems for identifying specific inhibitors for protein kinase C-related kinases (PRKs) for the searching for, or screening for, substances which are suitable high specificity inhibitors for protein kinase C-related kinases (PRKs). A use of such assays may not only be proposed for searching or screening purposes so as to find new substances suitable as inhibitors for PKRs, but may also be proposed for medical use, pharmaceutical or pharmacological use, food chemistry or animal food use, cosmetic testing use etc.

The invention is further exemplified by the following working examples which are explaining the invention but should not be construed to limit the invention.

EXAMPLE 1

AR-NTD Phosphorylation Assay

It could be shown in the prior art (E. Metzger et al.; loc. cit.) that the transcriptional activity of the androgen receptor can be regulated, in addition to influences exerted by androgen receptor ligands, by signalling by protein kinase C-related kinases (PRKs). As was found in accordance with the present invention, PRK1 phosphorylates the N-terminal domain (NTD) of the androgen receptor (AR) in vitro, thereby effecting an activation of the AR. This reaction offers a basis for one of the sub-assays of the assay system of the invention, i. e. the AR-NTD phosphorylation assay. Reference is made to FIG. 1.

Transfection of PRK1 in 293 cells and immunoprecipitation was performed as described in E. Metzger et al., loc. cit. Cell lysis and immunoprecipitation of PRK1 was performed in 50 mM Hepes pH 7,4; 100 mM NaCl; 50 mM NaF; 5 mM β-glycerophosphate; 2 mM EDTA; 2 mM EGTA; 1 mM NaV; 1% v/v NP40. myc-ΔNPRK1 was immunoprecipitated from 293 cell extracts in the presence of the specific a-myc antibody (lanes 1 and 3 in FIG. 1) or the non specific mIgG (lane 2 in FIG. 1). $E.\ Coli$ purified GST-AR-NTD was treated in the presence of the constitutive active PRK1 (myc-ΔNPRK1) and [γ-p32]. The phosphorylation reaction was performed for 20 min in 50 mM Hepes pH 7,4; 0.75 mM EGTA; 1.65 mM $MgCl_2$; 125 mM ATP/1mCi γp32ATP. Phosphorylation of GST-AR-NTD (* in FIG. 1) was detected by separation on a 10% SDS/PAGE gel. The control, $E.\ Coli$ purified GST protein was not phosphorylated by PRK1 (lane 3 in FIG. 1). The PRK1 used in this experiment is active, as determined by the specific auto-phosphorylation detected in lane 1 and 3 of FIG. 1.

As can be seen from FIG. 1, a phosphorylation of the NTD of the androgen receptor could be achieved successfully by PRK1. A specific inhibitor of PRK1 would not allow such a phosphorylation reaction to proceed smoothly and would thereby block the phosphorylation of the AR. Hence, the AR-NTD phosphorylation test would be a sensitive test for the specificity of the inhibition of PRK1 especially and of PRKs in general.

EXAMPLE 2

In another preferred embodiment, the assay system comprises the reaction of the ligand-dependent activation of the androgen receptor (AR) by RhoA V 14. It could be shown that, in the case of the androgen receptor, the RhoA V 14-mediated activation is dependent upon the presence or absence of an androgen receptor (AR) agonist as, for example, R1881. PRKs are involved in such an activation of the AR in the sense of an activation or promotion, and an inhibition by a potent inhibitor would reliably block such an activating or promoting action of the PRKs. Reference is made, in this respect, to FIG. 2.

293 cells were transfected with MMTV-LUC reporter and RhoA V14 expression plasmids, with or without the androgen receptor agonist R 1881 (concentration: $10^{-10}$ M) and treated with $5 \times 10^{-7}$ M Ro31-8220 or $3 \times 10^{-5}$ M HA 1077.

From FIG. 2, it can be seen that, in the presence of the inhibitors (almost in-dependent from an induction by R 1881), a considerable blocking of the ligand-dependent activation of the AR occurred. It could be shown by said use of the known inhibitors Ro31-8220 and HA 1077 that such a reaction "cascade" can be used as the basis for an assay on the inhibitory potency of inhibitors towards PRKs: The above two PRK inhibitors abolished agonist-dependent androgen receptor (AR) activation by RhoA V14.

EXAMPLE 3

In a further preferred embodiment of the invention, the assay system comprises the reaction of promotion of the androgen receptor agonist-induced cell proliferation by the androgen receptor.

The inventors studied the cell proliferation inter alia in MCF-7 cells which is induced by the androgen receptor agonist R 1881 under the activating/promoting action of PRKs. MCF-7 cells were cultivated in RPMI 1640 supplemented with 2 g/l $NaHCO_3$, L-Glu, Pen/Strep, 10% FCS (fetal calf serum), and insulin 1U/ml in the presence or absence of R1881 and Ro31-8220 at the indicated concentrations. The cell proliferation assay was performed according to the manufacture's instructions (Roche, #1647229). The results are shown in FIG. 3.

It could be shown by use of a known inhibitor of PRKs, Ro31-8220, that such a reaction "cascade" is inhibited by the inhibitor action on PRK and, hence, that such inhibitor action can be used as a basis for an assay on the inhibitory potency of inhibitors towards PRKs.

What is claimed is:

1. A process for determining whether a substance is a specific inhibitor of a protein kinase C-related kinase (PRK), wherein the process comprises selecting a substance to be tested for its PRK-related inhibitory activity;

providing at least one plurality of identical reaction mixtures which comprise at least one PRK, androgen receptor (AR), and RhoA V14 and allowing the at least one PRK to exert at least one measurable effect in the identical reaction mixtures under physiological conditions, the at least one measurable effect comprising a RhoA V14 dependent activation of the AR by the PRK;

combining each of the plurality of identical reaction mixtures with a different amount of the substance to be tested;

determining the at least one measurable effect as a function of the concentration of the substance to be tested in the reaction mixture and establishing that the substance is a specific inhibitor of the at least one PRK if an inhibitory effect of the substance on the RhoA V14 dependent activation of the AR by the PRK is detected.

2. The process of claim 1, wherein the at least one PRK comprises at least one of PRK1, PRK2 and PKNβ.

3. The process of claim 2, wherein the at least one PRK comprises PRK1.

4. The process of claim 1, wherein the at least one measurable effect is provided by least two reactions in which the at least one PRK exerts a measurable effect under physiological conditions and which are independent from each other.

5. The process of claim 3, wherein the at least one plurality of identical reaction mixtures provides a phosphorylation of an N-terminal domain of an androgen receptor (AR-NTD) by PRK1.

6. The process of claim 1, wherein the at least one measurable effect comprises a ligand-dependent activation of the AR by RhoA V14.

7. The process of claim 1, wherein the process comprises a promotion of an AR agonist-induced cell proliferation by the AR.

8. The process of claim 1, wherein the inhibitory effect of the substance is manifested by a disappearance of the RhoA V14 dependent activation of the AR by the PRK.

9. The process of claim 1, wherein the substance has an $IC_{50}$ value of <10 nM.

10. A process for determining whether a substance is a specific inhibitor of protein kinase C-related kinase PRK1, wherein the process comprises
    selecting a substance to be tested for its PRK1-related inhibitory activity;
    providing at least one plurality of identical reaction mixtures which comprise PRK1, androgen receptor (AR), and RhoA V14 and allowing the PRK1 to exert at least one measurable effect in the identical reaction mixtures under physiological conditions, the at least one measurable effect comprising a RhoA V14 dependent activation of the AR by the PRK1;
    combining each of the plurality of identical reaction mixtures with a different amount of the substance to be tested;
    determining the at least one measurable effect as a function of the concentration of the substance to be tested in the reaction mixture and establishing that the substance is a specific inhibitor of the PRK1 if an inhibitory effect of the substance on the RhoA V14 dependent activation of the AR by the PRK1 is detected.

11. The process of claim 10, wherein the at least one measurable effect is provided by least two reactions in which the PRK1 exerts a measurable effect under physiological conditions and which are independent from each other.

12. The process of claim 10, wherein the at least one plurality of identical reaction mixtures provides a phosphorylation of an N-terminal domain of an androgen receptor (AR-NTD) by PRK1.

13. The process of claim 10, wherein the at least one measurable effect comprises a ligand-dependent activation of the AR by RhoA V14.

14. The process of claim 10, wherein the process comprises a promotion of an AR agonist-induced cell proliferation by the AR.

15. The process of claim 10, wherein the inhibitory effect of the substance is manifested by a disappearance of the RhoA V14 dependent activation of the AR by the PRK1.

16. The process of claim 10, wherein the substance has an $IC_{50}$ value of <10 nM.

* * * * *